United States Patent [19]

Trick

[11] Patent Number: 4,483,331
[45] Date of Patent: Nov. 20, 1984

[54] ROD-TYPE PENILE IMPLANT

[75] Inventor: Robert E. Trick, Racine, Wis.

[73] Assignee: Medical Engineering Corporation, Racine, Wis.

[21] Appl. No.: 418,695

[22] Filed: Sep. 16, 1982

[51] Int. Cl.³ .............................................. A61F 5/00
[52] U.S. Cl. .................................................... 128/79
[58] Field of Search .................................. 128/79; 3/1

[56]     References Cited
     U.S. PATENT DOCUMENTS

| | | | |
|---|---|---|---|
| 3,176,316 | 4/1965 | Bodell | 3/1 |
| 3,879,767 | 4/1975 | Stubstad | 128/DIG. 21 |
| 3,886,600 | 6/1975 | Kahn et al. | 128/DIG. 21 |
| 3,893,456 | 7/1975 | Small et al. | 128/79 |
| 3,987,789 | 10/1976 | Timm et al. | 128/79 |
| 3,991,752 | 11/1976 | Gerow | 128/79 |
| 4,066,073 | 1/1978 | Finney et al. | 128/79 |
| 4,151,840 | 5/1979 | Barrington | 128/79 |
| 4,177,805 | 12/1979 | Tudoriu | 128/79 |
| 4,411,260 | 10/1983 | Koss | 128/79 |

*Primary Examiner*—Dalton L. Truluck
*Attorney, Agent, or Firm*—Quarles & Brady

[57] ABSTRACT

In an improved rod-type penile implant having a relatively stiff proximal portion for positioning inside the corpus cavernosum adjacent the pubis for supporting the implant, a longer relatively stiff distal portion for positioning in the corpus cavernosum of the pendulous penis and a hinge separating the distal and proximal portions, the improvement which comprises a distal portion including a reinforced inner core having a main body of relatively stiff material which is united to an outer tubular sleeve of fabric having a relatively high tensile strength so that the main body and fabric sleeve act together to increase the stiffness of the inner core.

1 Claim, 5 Drawing Figures

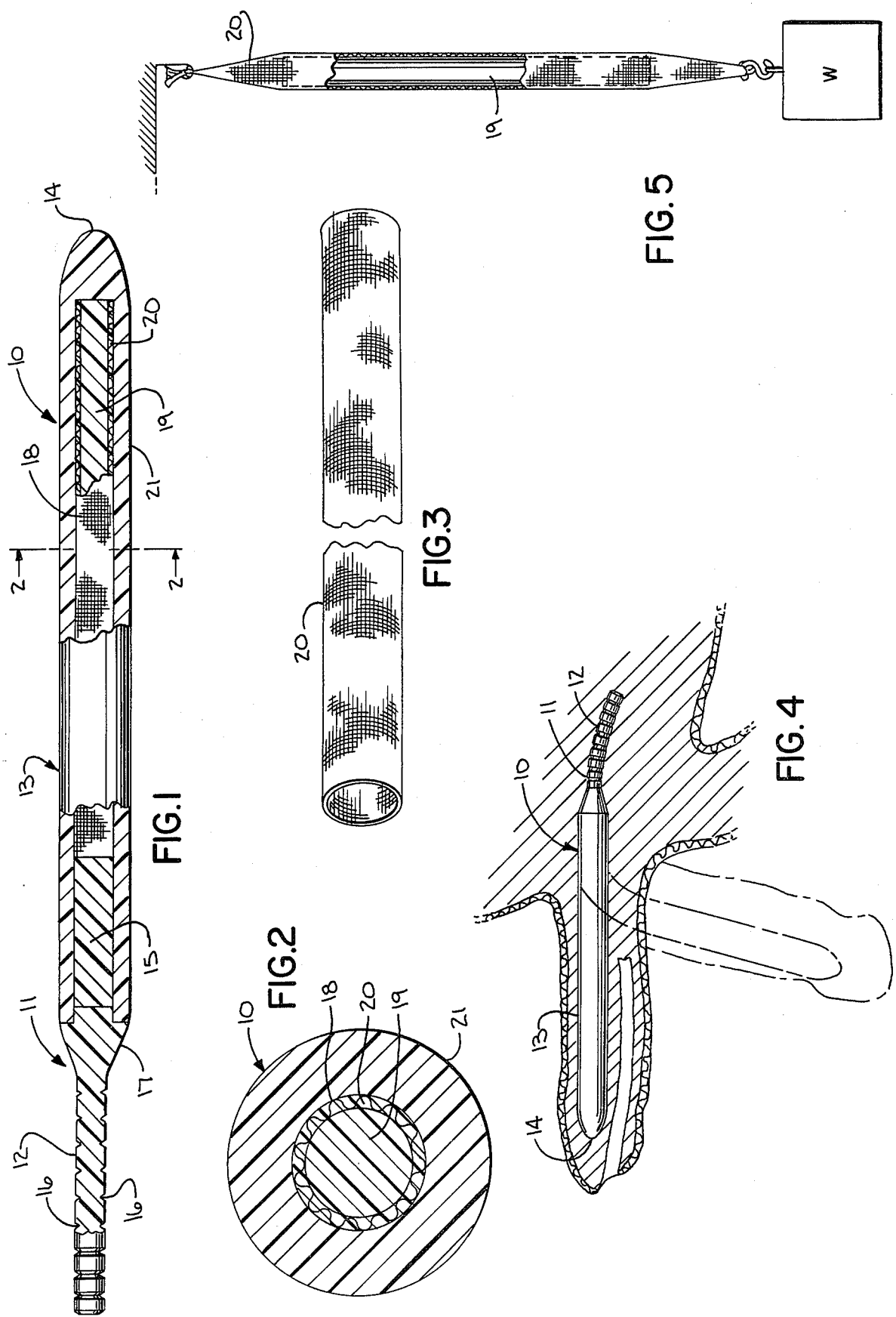

ROD-TYPE PENILE IMPLANT

FIELD OF THE INVENTION

The present invention relates to a novel penile implant which can be used in the treatment of erectile impotence. More particularly, it relates to an improved rod-type penile implant.

BACKGROUND OF THE INVENTION

There are instances of erectile impotence in which the patient does not respond to more conventional therapy, and the surgical implanting of a penile prosthesis is the only practical means of remedying the impotency.

The most common type of implantable penile prosthesis is a pair of identical rods of suitable stiffness. Each of the rods is surgically implanted into a corpus cavernosum of the penis. The implant disclosed in U.S. Pat. No. 4,066,073 is a rod-type penile prosthesis of considerable popularity which has a relatively stiff proximal portion for anchoring the implant, a relatively stiff and longer distal portion for implanting in the pendulous penis and a flexible hinge joining the two portions.

In U.S. Pat. No. 4,201,202 an implant is disclosed which is a combination rod and inflatable prosthesis. The prosthesis consists of a pair of rods, preferably of the type disclosed in U.S. Pat. No. 4,066,073, which has a flexible sleeve positioned and sealed axially about an intermediate portion of the rod to form a chamber for pressurizing fluid. Each of the implants has a pressure bulb of pressurizing fluid connected by tubing to the chamber so that it can be pressurized and also a valve to depressurize the chamber. A penile erection is achieved by either pressurizing the chambers if a soft rod is used or by manually moving the implants to an erect position if a stiffer hinged rod is used. The implant has an advantage over the conventional rod implant in that the chamber can be pressurized to increase penile girth.

SUMMARY OF THE INVENTION

It is the general object of the present invention to disclose an improved rod-type penile implant with a distal portion of increased stiffness and good resiliency.

The improved rod-type penile implant of the present invention is similar to the implant of U.S. Pat. No. 4,066,073 in that it has a relatively stiff proximal portion for positioning inside the corpus cavernosum adjacent the pubis for supporting the implant, a longer distal portion for positioning in the corpus cavernosum of the pendulous penis and a flexible hinge separating the distal and proximal portions. It differs from the patented implant in that the distal portion includes an inner core having a main body of relatively stiff material which is reinforced with a tubular sleeve of fabric having a high tensile strength. The tubular sleeve of fabric is united to or embedded in the material of the core so that the fabric sleeve and the main body of the core act together to increase the stiffness to the distal portion without decreasing its resiliency. The tubular sleeve increases the tensile strength of selective areas of the distal portion converting the distal portion to a form of reinforced beam. As a result, deflections due to loads are decreased without a decrease in resiliency. In the preferred embodiment, DACRON fabric is used, but other fabrics with good tensile strength can also be employed.

BRIEF DESCRIPTION OF THE DRAWINGS

FIG. 1 is a partial cross sectional view of a preferred embodiment of the penile implant of the present invention;

FIG. 2 is a cross sectional view taken along line 2—2 in FIG. 1;

FIG. 3 is a perspective view of the tubular fabric sheath of the embodiment of FIG. 1;

FIG. 4 shows generally the positioning of the implant within the penis and pubic area; and FIG. 5 is a schematic view showing a method of prestressing fabric for the preparation of a reinforced core.

DESCRIPTION OF THE PREFERRED EMBODIMENT

A penile prosthesis utilizing the implants of the present invention normally will consist of two separate and identical implants, each of which is implanted in a separate corpus cavernosum of a penis. However, for purposes of description herein, only one implant will be described.

As seen in FIG. 1, the penile implant of the present invention is identified by the numeral 10. Implant 10 includes a short proximal portion 11 which is constructed of a relatively stiff physiologically inert material such as medical application silicone rubber. At one end the proximal portion 11 has a short stem 12 which is implanted in the root end of the corpus cavernosum to support and anchor the implant 10. The implant 10 also includes a longer distal portion 13 with a conical tip 14. The distal portion 13 is implanted into the portion of the corpus cavernosum in the pendulous penis when the implant is in position as shown in FIG. 4. The proximal portion 11 and distal portion 13 are separated by a flexible hinge 15.

The entire penile implant 10 may be formed of a physiologically inert material such as medical grade, silicone rubber. The stiffness of the rubber may be controlled by the type and amount of catalyst used to cure the elastomer and the amount of heat and time employed during the curing or vulcanizing process.

While the term "stiff" is used in this specification and in the claims as a convenient and generally understood description of the desired physical properties of implant 10 and its various portions, a more precise, technical term is flexural modulus; that is, the ratio of applied force to resulting deflection. However, most tables of properties do not describe the stiffness properties or the flexural modulus for rubber-like materials. Rather they list related properties, such as hardness and tensile strength. These qualities are, therefore, used in the following description.

Hardness may be measured by a durometer, such as a Shore A durometer which ascertains the depth of penetration of a specified indentor into a specimen under specified conditions. A scale is chosen so that zero represents a material showing no measurable resistance to indentation and 100 represents a material showing no measurable indentation.

Tensile strength is the unit stress which produces failure of a specimen in tension.

In the preferred embodiment the proximal portion 11 of implant 10 is approximately 8–14 cm in length. The major length of portion 11 is the stem 12 which is approximately 6 mm in diameter. Stem 12 may contain axially spaced grooves 16 which assist in trimming proximal portion 11 to the correct length during surgery. A truncated conical section 17 increases the diameter of proximal portion 11 from that of stem 12 to the diameter of hinge portion 15 and distal portion 13 which are approximately 12 mm in diameter. Proximal portion 11 may be formed of a silicone rubber having a medium stiffness, for example, a Shore A hardness of 55±5 and a minimum tensile strength of 1000 psi.

Distal portion 13 contains a reinforced inner core 18. The main body 19 of the inner core 18 may be formed of material as stiff or stiffer than proximal portion 11. For example, material having a Shore A hardness of 70 or higher may be used. The main body 19 is covered with a tubular fabric sleeve 20 which is united to the body 19, preferably with a silicone sealant or adhesive, thus becoming an integral part of the inner core 18. The reinforced inner core 18 is covered with an outer sheath 21 of very soft material which produces a natural feel and helps when it is implanted to protect the overlying tissues from damage which might occur from external trauma. The overall diameter of distal portion 13 is approximately 12 mm. The length of distal portion 13 varies with the patient, lengths in a range of 6 to 12 cm being typical. The sheath 21 also includes the tip 14 which is typically conical or paraboloidal in shape to enhance the physiological compatibility of implant 10. The increased stiffness of the reinforced core 18 permits its diameter to be decreased, thus permitting the thickness of sheath 21 to be increased and improving the natural feel of the implant. Sheath 21 also extends over the hinge 15.

The rubber of sheath 21 and the hinge 15 may have a Shore A hardness of, for example, 20. The softness of this material and the small size of the hinge portion 15 prevents the development of meaningful tensile strength figures. Rather, the tensile modulus at 100 percent elongation for a solid rod of the material of hinge 15 which is 12 mm in diameter may be determined. A desirable modulus is 20 to 30 psi. Hinge portion 15 is approximately 4 cm long.

In the preferred embodiment, to form the penile implant 10, the sheath 21 is molded of soft rubber material. As noted supra, sheath 21 is closed at one end and formed with a tip 14 at the other end to fit the end of the corpus cavernosum. The open end of the sheath 21 may be trimmed to vary the length of distal portion 13 of implant 10. The main body 19 of the core 18 is formed by molding or extrusion and trimmed in accordance with the length of the distal portion of the implant being produced and placed within the tubular fabric sleeve 20. The sleeve 20 and main body 19 combination is then coated with silicone elastomer or other suitable sealing compound or adhesive to unite the fabric sleeve 20 to the main body 19 and the combination is cured to form the integral reinforced core 18. The thus formed core 18 is inserted and cemented in the interior of sheath 21. The central portion or hinge 15 molded or formed of soft bendable material is then inserted and cemented in the remaining length of sheath 21. If desired, the hinge 15 and reinforced core 18 may be attached to each other before inserting them into the sheath 21.

If greater stiffness in the distal portion 13 is desired, a stiffer reinforced core 18 can be made by first prestressing the fabric sleeve 20 and then uniting it to or embedding it in the main body 19. This can be readily done by placing the main body 19 within a longer sleeve of fabric which has ends which extend past the ends of the main body. Both ends of the sleeve may then be closed and the sleeve hung from a hook at the top with a predetermined weight attached to the lower end of the sleeve to exert a stretching force on the sleeve, as seen in FIG. 5. The prestressed sleeve 20 and main body 19 are then coated with silicone elastomer or adhesive to bind the sleeve 20 to the main body 19 and the combination cured. The excess fabric of the sleeve 20 is then trimmed away to obtain a reinforced core 18 which may be used in the manner previously described.

Although in the drawings a single penile implant 10 is shown, as previously described, a complete penile prosthesis will normally include two separate identical penile implants each of which is surgically implanted in a separate corpus cavernosum of the penis.

When properly implanted the stem 12 of the support portion 11 of the implant 10 is positioned in the root end of the corpus cavernosum near the pubic bone to anchor the implant 10, and the distal portion 13 and paraboloidal tip 14 is positioned in the glans end of the corpus cavernosum. As a result, the implants are positioned correctly in the corpus cavernosum of the penis and the likelihood of displacement is minimized.

The preferred method of implantation of the implants is through the perineum. After appropriate incision, the corpus cavernosum is dilated distally and proximally to accept the implant. The appropriate anatomical measurements are made to insure that the stem of the support portion is positioned at the base of the penis below the pelvic bone. An implant having an appropriate girth and length is selected and the tip portion inserted into the glans end of the corpus cavernosum of the penis with the tip positioned in the distal end of the corpus cavernosum. The stem of the support portion may then be trimmed to the desired length and inserted into the root end of the corpus cavernosum. The identical procedure is performed on the other side of the penis and the incision closed to complete the surgical procedure. The stems of the two implants preferably diverge laterally to accommodate the anatomy and provide lateral stability to the penis.

The penile implant of the present invention may also be employed as the rod portion of a combination rod and inflatable type implant such as that disclosed in U.S. Pat. No. 4,201,202.

It will be readily apparent to those skilled in the art that a variety of changes and modifications might be made without departing from the spirit and scope of the invention. For example, the distal portion could be constructed by placing the reinforcing fabric sleeve about the main body of the core and then covering the combination with relatively soft elastomer or plastic material to both unite the sleeve to the main body and to form the soft outer covering or sheath. Furthermore, in place of the tubular sleeve of reinforcing fabric, in some instances, it may be desirable to use a perforated tube of material of the desired tensile strength; therefore, the term "fabric" as used herein is intended to cover such a tube. It is to be understood that the scope of the invention is not to be limited except by the claims which follow:

I claim:

1. In an improved rod-type penile implant having a relatively stiff proximal portion for positioning inside the corpus cavernosum adjacent the pubis for supporting the implant, a longer distal relatively stiff portion for positioning in the corpus cavernosum of the pendulous penis and a hinge separating the distal and proximal portions, the improvement which comprises a distal portion having an inner core consisting of a main body which is united to and reinforced by an outer tubular fabric sleeve which has a relatively high tensile strength and which was first stretched and prestressed and then united to the main body while still in a prestressed condition.

* * * * *